United States Patent
Vallero (10) Patent No.: US 8,121,696 B2
(45) Date of Patent: Feb. 21, 2012

(54) TOPICAL ANALGESIA USING ELECTRICAL AND VIBRATION STIMULI

(75) Inventor: Rommel P. Vallero, Davis, CA (US)

(73) Assignee: Rommel P. Vallero, Davis, CA (US)

( * ) Notice: Subject to any disclaimer, the term of this patent is extended or adjusted under 35 U.S.C. 154(b) by 1067 days.

(21) Appl. No.: 12/017,324

(22) Filed: Jan. 21, 2008

(65) Prior Publication Data
US 2008/0188779 A1 Aug. 7, 2008

Related U.S. Application Data

(60) Provisional application No. 60/887,827, filed on Feb. 2, 2007.

(51) Int. Cl.
*A61N 1/34* (2006.01)
(52) U.S. Cl. .......................................... 607/46
(58) Field of Classification Search .................. 607/46
See application file for complete search history.

(56) References Cited

U.S. PATENT DOCUMENTS

| | | |
|---|---|---|
| 2,258,857 A | 10/1941 | McCann |
| 3,620,209 A | 11/1971 | Kravitz |
| 3,911,930 A | 10/1975 | Hagfors et al. |
| 4,010,742 A | 3/1977 | Kim |
| 4,177,817 A | 12/1979 | Bevilacqua |
| 4,289,136 A | 9/1981 | Rienzo, Sr. |
| 4,458,696 A | 7/1984 | Larimore |
| 4,782,837 A | 11/1988 | Hogan |
| 4,784,142 A | 11/1988 | Liss |
| 4,989,605 A | 2/1991 | Rossen |
| 5,366,489 A | 11/1994 | Burgio |
| 5,423,874 A | 6/1995 | D'Alerta |
| 5,496,363 A | 3/1996 | Burgio et al. |

(Continued)

FOREIGN PATENT DOCUMENTS

EP 1044624 10/2000

(Continued)

OTHER PUBLICATIONS

Sluka KA, Walsh D., Transcutaneous electrical nerve stimulation: basic science mechanisms and clinical effectiveness, J Pain. Apr. 2003;4(3):109-21.

(Continued)

*Primary Examiner* — Carl H Layno
*Assistant Examiner* — Jennifer Stewart
(74) *Attorney, Agent, or Firm* — Faegre Baker Daniels LLP (57) ABSTRACT

The present invention is an electrode with one or more conductive surfaces and one or more access windows allowing needles, lancets and other similar objects to pass through or near the electrode and into the underlying skin layer. The electrode adheres to skin and surrounding mild electrical and vibration stimulation acts to mask the pain signals caused when sharp objects penetrate the skin. The stimulation is delivered by an attachable electrical unit designed to generate both the TENS and vibration stimuli while connected to the electrode. In addition, a flap which is attached to the electrode may serve as a bandage type dressing by flipping down over the access window(s) once the procedure is done. The present invention is an electrode with one or more electrically isolated conductive surfaces coupled to a TENS and vibration generating unit. It is designed to allow access to underlying skin and is meant to be easily produced, with the electrode being disposable after each patient use.

28 Claims, 2 Drawing Sheets

U.S. PATENT DOCUMENTS

| | | | |
|---|---|---|---|
| 5,569,166 A | 10/1996 | Stone | |
| 5,776,170 A | 7/1998 | MacDonald et al. | |
| 5,797,966 A | 8/1998 | Bontoux et al. | |
| 5,904,712 A | 5/1999 | Axelgaard | |
| 6,086,572 A | 7/2000 | Johnson et al. | |
| 6,134,480 A | 10/2000 | Minogue | |
| 6,135,953 A | 10/2000 | Carim | |
| 6,231,531 B1 | 5/2001 | Lum et al. | |
| 6,415,177 B1 | 7/2002 | Tuan | |
| 6,493,592 B1 | 12/2002 | Leonard | |
| 6,516,226 B1 | 2/2003 | Bishay | |
| 6,741,889 B1 | 5/2004 | Holcomb | |
| 6,871,099 B1 | 3/2005 | Whitehurst | |
| 6,902,554 B2 | 6/2005 | Huttner | |
| 6,904,324 B2 | 6/2005 | Bishay | |
| 6,907,299 B2 | 6/2005 | Han | |
| 7,184,830 B2 | 2/2007 | Echt et al. | |
| 7,686,773 B2 * | 3/2010 | Lindquist ................ | 601/2 |
| 2002/0013602 A1 | 1/2002 | Huttner | |
| 2002/0019652 A1 | 2/2002 | Da Silva | |
| 2003/0181960 A1 | 9/2003 | Carter | |
| 2003/0187490 A1 | 10/2003 | Gliner | |
| 2003/0195599 A1 | 10/2003 | Bishay | |
| 2004/0015188 A1 | 1/2004 | Coulter | |
| 2004/0138712 A1 | 7/2004 | Tamarkin et al. | |
| 2004/0186466 A1 | 9/2004 | Chornenky et al. | |
| 2004/0220622 A1 | 11/2004 | Bernabei | |
| 2005/0038463 A1 | 2/2005 | Davar | |
| 2005/0089861 A1 | 4/2005 | Allen | |
| 2005/0149145 A1 | 7/2005 | Coulter | |
| 2005/0165459 A1 | 7/2005 | Coulter | |
| 2005/0177071 A1 | 8/2005 | Nakayama et al. | |
| 2005/0177201 A1 | 8/2005 | Freeman | |
| 2005/0181341 A1 | 8/2005 | Ewing et al. | |
| 2006/0206164 A1 | 9/2006 | Gavronsky | |
| 2007/0219470 A1 | 9/2007 | Talish et al. | |
| 2007/0282400 A1 | 12/2007 | Gorham | |
| 2011/0022115 A1 * | 1/2011 | Salzhauer et al. ............ | 607/46 |

FOREIGN PATENT DOCUMENTS

| | | |
|---|---|---|
| JP | 09299482850 | 11/1997 |
| KR | 0135345 | 4/1998 |
| KR | 0186876 | 4/1999 |
| KR | 200173746 | 3/2000 |
| WO | WO 2005/014105 | 2/2005 |
| WO | WO 2005/065770 | 7/2005 |

OTHER PUBLICATIONS

Kundu S, Achar S., Principles of office anesthesia: part II. Topical anesthesia, Am Family Physician, Jul. 1, 2002;66(1):99-102.

Jacobson RM, et al., Vaccine Research Group. Making vaccines more acceptable, Vaccine, Mar. 21, 2001;19(17-19):2418-27.

Electrotherapy Stds. Committee: Electrotherapeutic terminology in physical therapy, Sec. on clinical electrophysiology and Amer. Phys. Therapy Assoc., Alexandria, VA, 2001.

Rushton DN, Electrical stimulation in the treatment of pain, Disabil Rehabil. May 20, 2002;24(8):407-15.

Melzack R, Wall PD: Pain Mechanisms: A new theory, Science 150:971-978, 1965.

Vibration Therapy for Pain, Lancet. Jun. 20, 1992; 339(8808):1513-4.

Koltzenburg,Handwerker, Differntial Ability of Human Cutaneous Nociceptors to Signal Mechanical Pain . . . , Journal of Neuroscience, Mar. 1984, 14(3) 1756-1765.

* cited by examiner

TOPICAL ANALGESIA USING ELECTRICAL AND VIBRATION STIMULI

CROSS-REFERENCE TO RELATED APPLICATIONS

The present application claims priority from Provisional U.S. Patent Application No. 60/887,827 filed on Feb. 2, 2007, and incorporated herein by reference.

FIELD OF THE INVENTION

The present invention relates to a method of reducing or eliminating the pain from injections and other similar procedures performed on skin by the application of TENS (Transcutaneous Electrical Nerve Stimulation) and vibration stimulation. More specifically, the invention relates to a specialized skin electrode and a connectable TENS/vibration generating unit used to deliver both types of stimulation to the electrode.

BACKGROUND OF THE INVENTION

TENS has been used for years as a noninvasive, inexpensive, and safe technique to help reduce acute and chronic pain. See, e.g., *Electrotherapy Standards Committee: Electrotherapeutic terminology in physical therapy*, Section on clinical electrophysiology and American Physical Therapy Association, Alexandria, Va., 2001, and Rushton D N, *Electrical stimulation in the treatment of pain*, Disabil Rehabil. 2002 May 20; 24(8):407-15, both of which are incorporated herein by reference.

Typically, the application of a low voltage, low current, mild electrical signal through electrodes placed on skin counteracts other separate nerve signals indicating pain or discomfort. Many studies have supported the gate control theory first described by Melzack et al. in 1965 to explain this physiological response. See, e.g., Melzack R, Wall P D: *Pain Mechanisms: A new theory*, Science 150:971-978, 1965, incorporated herein by reference.

Briefly stated, pain is elicited when noxious stimuli trigger specific nerve endings in the skin. Pain impulses are then transmitted by small diameter nerve fibers through the spinal cord and to the brain. Gate theory states that there is a gating mechanism in the dorsal horn area of the spinal cord that may act to inhibit the transmission of pain signals to the brain. The gate may be closed by simultaneous stimulation of other larger diameter sensory nerve fibers using non-painful stimuli. Practical application of the gate control theory has lead to widespread use of TENS for pain control. TENS stimulates large diameter sensory nerve fibers with mild repetitive electrical impulses via electrodes applied to the skin. This stimulation acts to close the gate in the dorsal horn and results in the inhibition of pain transmission.

Similarly, vibration therapy is a safe and effective technique, which has long been used to alleviate pain. See, e.g., *Vibration Therapy for Pain*, Lancet. 1992. Jun. 20; 339(8808):1513-4, incorporated herein by reference. Like TENS, vibration provides another type of non-painful stimulus, which may be used to attenuate the transmission of pain signals by using the gating mechanism described above. Some sensory receptors, like those that sense vibration, are located deeper down in the skin layer and may not be fully stimulated by the superficial current of TENS alone. Vibration therapy and TENS used together may be able to more completely stimulate the sensory receptors found in the skin and result in a more effective blocking of pain signals.

In addition to the physiological mechanism of pain reduction described above, both TENS and vibration stimuli around the procedure site may also act as a form of distraction, making it more difficult to identify exactly where and/or when a painful stimulus occurs.

Commercially available electrodes for TENS therapy come in the form of small electrically conductive patches of different sizes and shapes that are applied directly to the skin and connected to a TENS device via wires. The TENS device is usually a compact self contained unit which is widely available commercially and produces electrical impulses of varying intensities and frequencies based on settings dialed into the unit. Two or more separate electrodes are usually applied to the skin in order to complete an electrical circuit. The electrodes are typically placed at or near the area of pain and used to help alleviate discomfort caused by deeper pain fibers such as those found on muscles and joints.

These types of electrodes have not been specifically designed to induce analgesia of the skin. The multiple separate electrodes are cumbersome to apply and often provide a much wider area of stimulation than is really needed for superficial analgesia. Commonly used electrodes also do not allow access to the underlying skin surface in order to perform procedures and other interventions. It may be highly advantageous if an electrode may deliver concentrated electrical stimulation at or near a potential injection site and at the same time allow access to the site. It may also be advantageous if vibration stimulation may also be delivered through this same electrode to act as additional stimuli for the attenuation of pain.

Painful injections into and through the skin for immunizations, medication administration, blood sugar testing, phlebotomy, IV placement, and the like, are usually done without the use of a local or topical anesthetic. This results in an unpleasant experience for most adults, and may be an extremely traumatic event for children or other sensitive persons. See, e.g., Jacobson R M, Swan A, Adegbenro A, Ludington S L, Wollan P C, Poland G A; Vaccine Research Group. *Making vaccines more acceptable—methods to prevent and minimize pain and other common adverse events associated with vaccines*, Vaccine, 2001 Mar. 21; 19(17-19):2418-27, incorporated herein by reference.

At times the fear or aversion to these types of procedures may lead to noncompliance of treatments and testing by adults and children alike. A device that reduces or eliminates the pain of these procedures may lead to increased compliance and benefit the overall health of many individuals.

Products to reduce the pain of injections and similar procedures do exist but have significant drawbacks and are not used often because of these limitations. Topical commercially available anesthetic creams such as EMLA (marketed by AstraZeneca) have a slow onset of action, requiring up to 90 minutes to be fully effective. See, e.g., Kundu S, Achar S., *Principles of office anesthesia: part II. Topical anesthesia*, Am Family Physician, 2002 Jul. 1; 66(1):99-102, incorporated herein by reference.

Ethyl chloride and other similar chemicals, long made available by corporations such as the Gebauer Company, act as a skin refrigerant to numb the skin prior to injections but the effects are short lived and its application is often more painful than the injection itself. Sontra Medical Corporation has a product called the Sonoprep that uses ultrasound to make the skin more permeable to anesthetic creams, but anesthesia still takes a full 5 minutes with this device. Similarly, B. Braun Medical Inc. markets a device called the LidoSite meant to address the pain of injections. This device uses TENS technology to drive topical anesthetics into the skin but still needs at least 10 minutes for full effect.

More recently, Anesiva's Zingo topical anesthetic was FDA approved August 2007 for IV cannulation and venipuncture pain. Anesiva claims effectiveness within about 2-3 minutes but even this is too long to wait considering a typical vaccine shot takes just a few seconds to administer. Another effective technique sometimes employed by experienced practitioners involves manually patting, vibrating, or stretching the skin around the site of injection just prior to a needle stick. This method is also meant to elicit the gating mechanism by using stimuli to mask the pain of injection, but the efficacy is very user dependent. It also leaves only one hand free to perform the injection or other procedure.

Bionix Corporation markets a device called the ShotBlocker, which is pressed onto the skin and uses local pressure to elicit the gating mechanism as described above. This product has multiple blunt tips surrounding a notch and requires one hand to push it against the skin. The fingers must be placed adjacent to the injection site and may be at risk for needle stick injury if unexpected movements occur. It also does not allow much variability in the quality or quantity of stimuli, which may be used to inhibit pain transmission.

Huttner, U.S. Pat. No. 6,902,554, incorporated herein by reference, describes a device which is pressed onto the skin and uses local pressure to elicit the gating mechanism as described above. This device requires one hand to push it against skin, again leaving only one hand available to inject or perform the needed procedure. It also does not allow much variability in the quality or quantity of stimuli, which may be used to inhibit pain transmission.

The following Prior Art references were discovered during a Prior Art search commissioned by applicant. All of these references, as well as the patents and other references cited in the present Specification, are expressly incorporated herein by reference.

Published U.S. Patent Application No. 2005/0149145, (Coulter, George Gary), incorporated herein by reference, discloses a pain reducing apparatus for use during therapeutic injection, (e.g. immunization), which has a current applying device coupled to current generating device for applying nerve stimulating current to electrodes placed around injection location.

Published U.S. Patent Application No. 2004/0015188, (Coulter, George Gary), incorporated herein by reference, discloses a therapeutic injection or sampling device and process which comprises a mechanism for generating electrical output for a Trans Epithelial Nerve Stimulating current and mechanism for applying to patient's body part.

European Patent No. 1699522, (COULTER, GEORGE GARY), incorporated herein by reference, discloses a hemorrhage reducing apparatus for use during therapeutic injection, which has electrodes placed around injection location on skin of patient, where voltage fed to electrodes affects C fibers in skin.

Published U.S. Patent Application No. 2005/0177201, (Freeman, Gary A), incorporated herein by reference, discloses insertion of a probe element through the skin to a penetration depth for treatment, which involves moving the probe element along a penetration depth in a series of incremental movements. In the field of acupuncture, pre-treatment of the insertion area with electrical energy, often in the form of high-frequency waveforms is typically used for transcutaneous electrical nerve stimulation (TENS), is employed to reduce the discomfort of insertion as well as provide optimal placement and treatment.

Published U.S. Patent Application No. 2003/0187490, (Gliner, Bradford Evan), incorporated herein by reference, discloses an annular electrode for neural stimulation, which has an annular outer contact enclosing area, which is several times greater than neural cell structure area.

Published U.S. Patent Application No. 2003/0181960, (Carter, John), incorporated herein by reference, discloses an electrotherapy apparatus for providing therapeutic electric current to a treatment site of a patient, which has a generator providing two pulsing electric alternating currents, a feed electrode and a return electrode.

U.S. Pat. No. 5,776,170 (MacDonald, Alexander John Ranald), incorporated herein by reference, discloses an electrical stimulation analgesia apparatus for electrotherapy, which supplies electrical pulses with rapid rising and falling phases to electrodes on body surface to stimulate analgesia effects in central nervous system.

U.S. Pat. No. 5,366,489 (Burgio, Paul A.), incorporated herein by reference, discloses an anesthesia electrode and applicator assembly for TENS, with active electrodes and return electrodes having a common carrier with a field of pressure sensitive adhesive for adhering electrode to the hand of practitioner or applicator.

U.S. Pat. No. 6,516,226 (Bishay, Jon M), incorporated herein by reference, discloses a percutaneous electrical therapy system, which has an electrode housing, which supports and guides an electrode in a correct way during insertion of the electrode.

U.S. Pat. No. 6,741,889 (Holcomb, Robert R), incorporated herein by reference, discloses an electromagnetic treatment device e.g. for pain and swelling which has an alternating polarity quadripolar array which generates a three dimensional steep field gradient to alter stability of excitable membranes to treat ailments.

Published U.S. Patent Application No. 2005/0089861, (Allen, John J), incorporated herein by reference, discloses lancing to obtain a sample of blood, which involves completely withdrawing the sharpened tip from incision, and drawing blood through the channel to the sensor. Sensor strip may be, for example, a glucose sensor strip which uses electrochemistry to measure the amount of glucose in a bodily fluid, such as, for example, blood or interstitial fluid.

Published U.S. Patent Application No. 2002/0019652, (Da Silva, Luiz B), incorporated herein by reference, discloses a sterile bandage is combined with a TENS device for use in covering a wound and providing electrical stimulation to promote healing and block pain.

U.S. Pat. No. 4,458,696 (Larimore, Franklin C), incorporated herein by reference, discloses a self-adhering TENS electrodes extensible with the skin, comprising body-conformable conductive adhesive and connector layers eliminate dry-out problems.

U.S. Pat. No. 6,871,099 (Whitehurst, Todd K), incorporated herein by reference, discloses a chronic pain e.g. migraine, treating method, involves providing operating power and stimulation parameters to stimulator to generate stimulation pulses based on parameters and delivering pulses to nerves and tissue.

U.S. Pat. No. 5,423,874 (D'Alerta, Mario), incorporated herein by reference, discloses an electronic patch for applying pain reducing electrical energy to a body, which has an electronic circuit formed in a patch for generating and delivering electrical energy through afflicted region on patient's body.

U.S. Pat. No. 5,904,712 (Axelgaard, Jens), incorporated herein by reference, discloses a transcutaneous medical electrode, which uses a grid of conductive arrays, each with selection of electrical connections to sections of arrays.

U.S. Pat. No. 4,177,817 (Bevilacqua, Albert J.;), incorporated herein by reference, incorporated herein by reference, discloses a transcutaneous stimulation pulse electrode assembly, which has two electrolyte-filled chambers between adhesive coated surfaces and electric contacts.

Published U.S. Patent Application No. 2002/0013602, (Huttner, James J.), incorporated herein by reference, discloses a method of controlling pain from surgical injections and minor medical procedures, which involves urging skin engaging surface of pressure member against skin of patient proximate the site.

U.S. Pat. No. 4,289,136 (Rienzo, Sr., Donald D.), incorporated herein by reference, discloses a percutaneous pain alleviation system, which produces variable amplitude right-angled sawtooth pulses at its two electrodes, and has output current control.

U.S. Pat. No. 4,989,605 (Rossen, Joel), incorporated herein by reference, discloses a pain treatment micro-current transcutaneous nerve stimulator, which uses a modulated monophasic sequence of bursts of DC carrier supplied to patient via electrodes.

U.S. Pat. No. 6,907,299, (Han, Shu-Chang), incorporated herein by reference, discloses an electrode for transcutaneous electric nerve stimulator which has a conductive element made of carbon fiber, whose impedance is less than specified value.

U.S. Pat. No. 6,904,324, (Bishay, Jon M.), incorporated herein by reference, discloses a percutaneous probe deploying apparatus to pierce the skin surface using electrodes for use in electrical nerve stimulation to treat pain in tissue.

Published U.S. Patent Application No. 2003/0195599, (Bishay, Jon M.), incorporated herein by reference, discloses a percutaneous probe deploying apparatus to pierce the skin surface using electrodes for use in electrical nerve stimulation to treat pain in tissue.

Published U.S. Patent Application No. 2006/0206164, (Gavronsky, Stas), incorporated herein by reference, discloses a percutaneous electrical nerve-stimulating device for electro-acupuncture, which has a needle/electrode holder including a linear electrode/needle guide channel, and pin electrode connecting needle/electrode to source of electric pulses.

U.S. Pat. No. 4,784,142, (Liss, Saul;), incorporated herein by reference, discloses an electronic dental analgesia method using electrodes on the head and gums to pass an electric wave through patients nerve system to suppress perceived pain.

U.S. Pat. No. 3,620,209 (Kravitz, Harvey), incorporated herein by reference, discloses a reusable vibrating electrical device, which is strapped onto the arm of a patient in order to attenuate the pain of an injection by delivering vibration stimuli around the injection site.

SUMMARY OF THE INVENTION

It is the object of the present invention to overcome some of the drawbacks of the prior art mentioned above and to provide a safe, reliable, easily employed method of inducing analgesia to the skin in order to minimize pain associated with injections, and other similar procedures.

The present invention comprises an electrode with one or more conductive surfaces and one or more access windows allowing needles, lancets and other similar objects to pass through or near the electrode and into the underlying skin layer. The electrode adheres to skin and surrounding mild electrical and vibration stimulation acts to mask the pain signals caused when sharp objects penetrate the skin. An attachable unit may generate both the TENS and vibration stimuli while connected onto the electrode. A flap attached to the electrode may serve as a bandage dressing by flipping down over the access window(s) once the procedure is done. The electrode may remain on the patient to act as a bandage and may be discarded later.

The placement of multiple conductive surfaces on one electrode has been described before by Burgio et al. (U.S. Pat. No. 5,496,363), incorporated herein by reference. However the electrode of Burgio was meant to induce intra oral anesthesia and was not designed to allow for sharp instruments to be passed directly through the electrode. Carim (U.S. Pat. No. 6,135,953) and Minogue (U.S. Pat. No. 6,134,480), both incorporated herein by reference, also describe multiple conductor skin electrodes. However these electrodes, like Burgio's, were not specifically designed for skin analgesia and do not allow direct access to the underlying skin for procedures.

Coulter (Published U.S. Patent Application Nos. US 20050165459 A1 and US 20050149145 A1, both of which are incorporated herein by reference,) describes a method of using TENS to reduce the pain of a therapeutic injection by placing an array of electrodes on the skin of a patient around an injection site. However, Coulter's patent application does not disclose placing these electrodes onto a single unit with multiple conductive surfaces. Thus, his method requires time-consuming application and removal of multiple and separate electrodes. Also, Coulter does not demonstrate the combined use of TENS and vibration stimulation and places a limit of five square millimeters for each of the electrodes. This small size and use of TENS alone limits the ability to stimulate sufficient numbers of large diameter sensory nerve fibers and does not take full advantage of the gating mechanisms described above.

In Published U.S. Patent Application No. US 20040015188, also incorporated herein by reference, Coulter describes another device utilizing two electrodes placed together onto a large apparatus that is pressed onto the skin to deliver TENS. The device includes the TENS unit and a means of holding a syringe. Alternatively, a device is also described within the same patent application that utilizes electrodes placed onto the palm surface of a glove. The glove is to be worn by the operator and the electrodes pushed up against the patient's skin in order to deliver TENS. Although these devices utilize multiple conductive surfaces arranged as a unit to deliver TENS prior to an injection, they too have limitations. Like Hunter's patent above, these devices must be actively held up against the skin and leaves only one hand available to inject or perform the needed procedure. These devices were also not designed to be disposable and may likely need time consuming sterilization procedures between each patient. The manufacture of such devices may also involve multiple parts and considerable assembly time, which may add to the costs of production.

In U.S. Pat. No. 3,620,209 Kravitz discloses a reusable vibrating electrical device, which is strapped onto the arm of a patient in order to attenuate the pain of an injection by delivering vibration stimuli around the injection site. Like some of the prior art above, this device does not adhere to the skin and is not disposable, resulting in similar limitations as discussed in the previous examples.

The present invention is specifically designed to provide compact electrical and vibration stimulation to the skin and allow access to the skin layer. The present invention is a single unit electrode with electrically isolated conductive areas coupled to a TENS and vibration generating unit. It is also designed to allow use of both hands to perform the procedure and the electrode itself is meant to be easily produced and disposable after each patient use. The TENS/vibration portion of the unit is meant to be easily re-used and, since it does not contact the skin, requires no special sterilization or cleaning between applications. Analgesia of the skin may be obtained almost immediately once the TENS/vibration unit is connected to the electrode and turned on. This is in contrast to topical anesthetic creams, which may have a delay of up to 90 minutes as discussed above.

BRIEF DESCRIPTION OF THE DRAWINGS

Please note that all figures, except FIG. 5, are drawn at 1:1 scale. Note, however, that other sizes for the electrodes may be used without departing from the spirit and scope of the present invention.

DETAILED DESCRIPTION OF THE INVENTION

Referring to FIGS. 1-5, the present invention comprises an electrode 10 comprising a non-conductive flexible backing 20 with two electrically conductive surfaces 30a and 30b mounted onto this backing and positioned close to each other at roughly opposing ends of the electrode. Conductive skin adhesive 40a and 40b of the type commonly found on commercially available electrodes are positioned over each conductive surface. The conductive surfaces and the conductive adhesive overlying these surfaces are separated from each other by a small space 50 or a strip of non-conductive material so that the surfaces remain electrically insulated from one another.

Each conductive surface and their associated conductive adhesive may be electrically continuous with a means of connecting the electrode to the TENS/vibration unit 15. The method of connection may be via ferromagnetic/electrically conductive discs, conductive buttons, conductive snaps, conductive adhesive, hook and loop fastener, or other connective means 100 which may allow the transmission of both TENS and vibration stimulation to the electrode. Within or between the conductive surfaces is a window 70 or orifice large enough to allow needles and similar sharp instruments to pass through the electrode and into the skin layer underneath. The selection of materials to construct the present invention may be similar to conventional electrodes and are well known to those skilled in the art of electrode construction.

Figure 1:
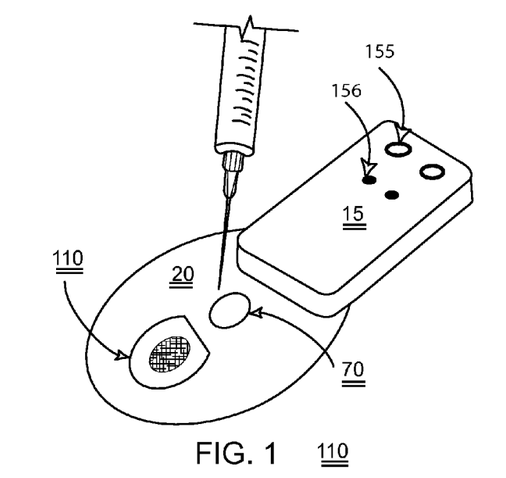
FIG. 1 is a perspective view of the first and preferred embodiment of the present invention.
Figure 2:
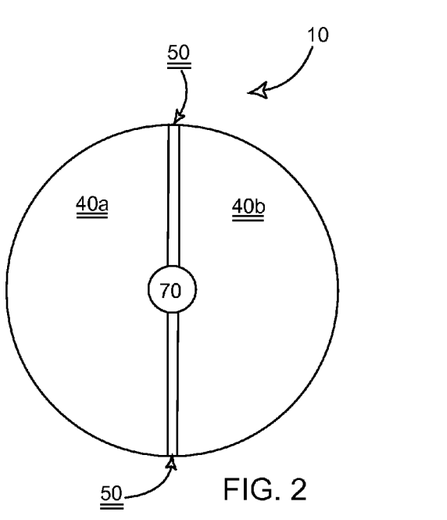
FIG. 2 is a bottom view of the first embodiment of the present invention.
Figure 3:
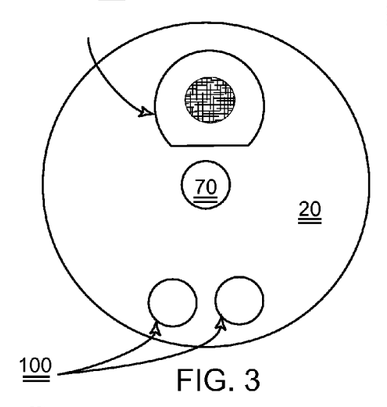
FIG. 3 is a top view of the first embodiment of the present invention.
Figures 4, 5:
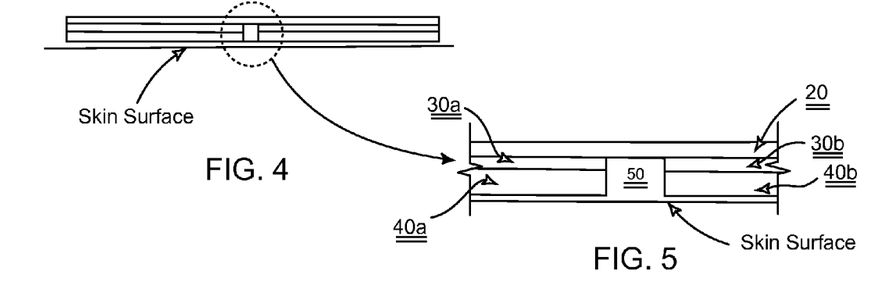
FIG. 4 is a side view of the first embodiment of the present invention.
FIG. 5 is a magnified side view of the first embodiment of the present invention.

Referring to FIG. 1, The TENS/vibration unit 15 is a separate electronic device, which is designed to attach to the electrode via various possible connective means, which may allow the transmission of both TENS and vibration stimulation to the electrode. Enclosed within the compact ergonomic casing is circuitry typical to that found in commercially available TENS generating units. This circuitry may have the ability to generate single or multiple frequency TENS stimuli and deliver this current to the electrode in parallel or in series. Variables such as frequency, current intensity, pulse width, and the like, may be made user adjustable.

Optionally included within the casing 15 is a means of creating the vibration stimuli. This may be accomplished by various means using rotational or oscillating vibration devices commonly found in cell phones and pagers, for example. One or more of these vibration devices may be placed in the unit depending on the application. Programmable micro controller circuitry similar to that found in many commercially available digital devices may also be enclosed within the unit to control the TENS and vibration stimuli. It may be pre-programmed to gradually increase both stimuli over a few seconds to a preset maximum level to prevent the initial sensation of surprise associated with a more sudden application of full electrical and TENS stimulation.

This micro controller may also be pre-programmed to deliver randomly timed bursts of electrical and/or vibration stimuli causing another form of distraction for the patient and making it more difficult to identify when the injection actually occurs. The micro controller may be programmed to deliver varying levels of TENS stimuli based on user input via small buttons 155 on the unit. For example, the user may be asked to press one button for low, medium or high intensity prior to application of the unit in order to deliver appropriate amounts of current to various age groups with differing sensitivity levels. Suitable membrane switches may be used to select the intensity and duration of electrical and vibration effect.

Alternately, wire, radio frequency (RF) or infrared control links may be used to provide a remote control so that the operator need not press directly onto the TENS/vibration unit. LEDs, or an LED display, video display or the like 156 may be used to indicate that the unit is operating, the batteries are charged or discharged, and also show the amount of electrical and vibration stimuli, and other data. This micro controller circuit may also be programmed to measure physiological variables via the electrode contacts such as resistance or capacitance of each individual's skin. These variables may be displayed on the display of the unit, or may be transmitted to other apparatus via data links (wired, RF, Infrared, or the like) so as to record patient data if required. Based on these brief initial readings, the micro controller may then deliver an appropriate amount of TENS or vibration stimulation.

The micro controller circuitry may also be used to identify different types of electrodes being used and then deliver a specific amount of stimuli based on that initial identification. For example, if the unit is connected onto a child type electrode, the unit may identify the specific electrode type via electrical or mechanical means unique to the electrode type and then deliver the correct amount of stimuli. The micro controller may also be pre-programmed so that the TENS and vibration stimuli begin once the unit is firmly attached to the electrode and stop when the unit is pulled away. This may eliminate the extra step of having to turn the unit on and off with every use. To power the entire unit, a small possibly rechargeable battery may also be enclosed within.

The invention described above is meant to reduce the pain experienced when needles and similar devices are inserted into skin. This unique electrode and TENS/vibration unit may be highly beneficial in alleviating pain due to immunizations, medication administration, phlebotomy, blood glucose checks, IV catheter placement, and the like. With minor changes in size and shape, this invention may be utilized for numerous other procedures as well.

Electrodes with the same basic features of the present invention may be shaped and sized to fit over specific body structures such as earlobes and fingers. The access window size and or shape may also be designed to accommodate different uses. Because of this, other medical applications may also benefit from this device including painful skin treatments such as laser therapy, skin biopsy, wart removal, splinter and hook removal, or any potentially painful procedure done at or near the skin surface. Of course the veterinary field may also benefit from the topical analgesic effects found useful in human subjects. The use of this device is not limited to medical procedures. Painful cosmetic procedures such as ear and body piercing, tattooing, and hair removal may also be made more comfortable with the present invention.

Commercially available electrodes have one conductive surface that may deliver only one circuit of electrical stimulation. Studies in the past have suggested that multiple specific electrical impulse frequencies may act to attenuate pain. See, e.g., Sluka K A, Walsh D., *Transcutaneous electrical nerve stimulation: basic science mechanisms and clinical effectiveness*, J Pain. 2003 April; 4(3):109-21, incorporated herein by reference.

Figure 6:
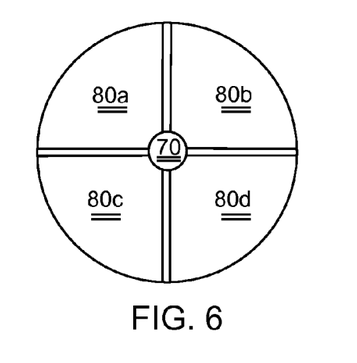
FIG. 6 is a bottom view of a second embodiment of the present invention.

Thus, it may be beneficial if a TENS electrode may deliver electrical stimulation of multiple different frequencies at the same time. Referring to FIG. 6, another embodiment of the present invention may have four conductive surfaces on one electrode 80*a*, 80*b*, 80*c*, and 80*d* surrounding an access window 70 which may allow simplified, concentrated, simultaneous application of multiple frequency electrical stimulation. Electrical stimulation of differing frequencies may also be delivered via two isolated conductive surfaces as in FIG. 2 and FIGS. 7 through 10.

Figure 7:
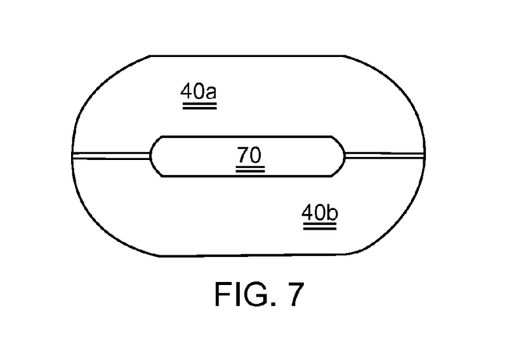
FIG. 7 is a bottom view of a third embodiment of the present invention.

Referring now to FIG. 7, window 70 between the conductive surfaces 40*a* and 40*b* may also be in the shape of an elongated rectangle, oval, or other similar shape to allow TENS to be used as a topical analgesic for small laceration repairs or for IV catheter placement.

Figure 8:
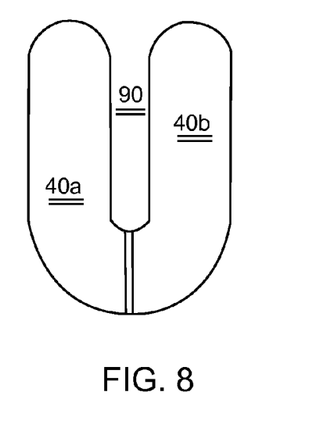
FIG. 8 is a bottom view of a fourth embodiment of the present invention.

Referring to FIG. 8, a notch 90, instead of a window may also be used to allow for more visualization of the skin area between conductive surfaces 40*a* and 40*b*.

Figure 9:
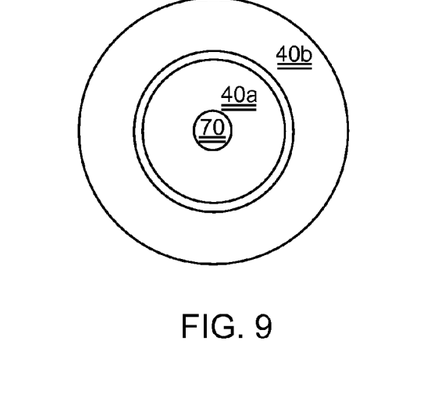
FIG. 9 is a bottom view of a fifth embodiment of the present invention.
Figure 10:
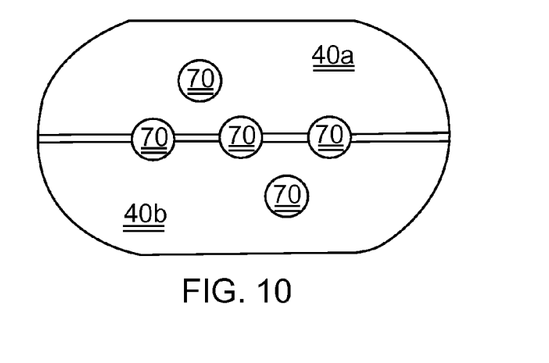
FIG. 10 is a bottom view of a sixth embodiment of the present invention.

Referring now to FIG. 9, the separate electrode conductive surfaces in the present invention may be arranged side by side as described above, in a concentric circular pattern around the access window 70, or any pattern that allows for the electrical isolation between the two conductive surfaces 40*a* and 40*b*. Referring to FIG. 10, the electrode may also be made with multiple windows 70 within or between the conductive surfaces 40*a* and 40*b* to allow for multiple injections such as those needed with immunizations or allergy testing.

Referring back to FIGS. 1 and 3, after a needle pierces the skin within the access window, an adhesive bandage flap with a gauze center 110 may be designed to flip down onto the skin within the window 70 to protect the site once the procedure is done. This may make it unnecessary to remove the electrode after a procedure in order to place a conventional bandage. The electrode serves as a bandage for the patient to help reduce bleeding, prevent infection, and aid in the healing process.

To help gain acceptance of the device by pediatric patients and to act as another form of visual distraction, the non-conductive backing of the electrode and/or the attached TENS/vibration unit may be printed with colors and/or shaped to resemble animals, cartoon characters, and the like.

Small colorful LEDs or other light sources having low power drain may also be placed on the electrode and/or TENS/vibration unit to offer yet another interesting distraction. A flat panel display, for example, may provide information about the operation of the device and also generate a distracting pattern or image so the patient is distracted from the procedure.

Similarly, circuitry may be included within the electrode and/or the attached TENS/vibration unit to emit sounds, music, spoken words, and the like, meant to serve as an auditory distraction. Licensed characters may present audio messages, for example, to encourage and distract children during the procedure. After the procedure, the patient may be encouraged to keep the electrode as a type of reward or "sticker" for getting his/her "shots" that day, and the electrode may serve as bandage as well. Licensed characters or other designs may appear on the electrode and/or TENS/vibration unit for decorative or amusement purposes.

A smaller electrode similar to the invention described above may also be employed to provide nerve block to the fingers. The electrode may be wrapped around the base of a finger with the conductive surfaces overlying the nerves on either side of the finger. This placement may provide analgesia over an entire digit, resulting in decreased pain from blood sugar testing, laceration repairs, and other similar procedures. Although illustrated generally in 1:1 scale, the electrodes of the present invention may be made in other sizes and shapes without departing from the spirit and scope of the present invention, for other applications and operations.

While the preferred embodiment and various alternative embodiments of the invention have been disclosed and described in detail herein, it may be apparent to those skilled in the art that various changes in form and detail may be made therein without departing from the spirit and scope thereof.

I claim:

1. A method for providing topical analgesia during a procedure, comprising:
   attaching an electrode to a patient's skin, the electrode having one or more conductive surfaces and at least one access point for allowing objects to pass through the at least one access point and into the patient's skin;
   attaching a module to the electrode;
   generating, using the module, electrical energy in order to deliver an electrical stimuli through the electrode to the patient's skin to provide an analgesic effect;
   generating, using the module, vibration to create a vibration stimuli through the electrode to the patient's skin to provide an additional analgesic effect; and
   flipping down a flap hinged to the electrode over the at least one access point to act as a bandage dressing after the procedure is completed, wherein the electrode and flap remain on the patient to act as a bandage.

2. The method of claim 1, wherein the electrode comprises:
   at least one electrically conductive layer for conducting the electrical stimuli from the module;
   at least one electrically conductive adhesive layer, for adhering the electrically conductive layer to the patient's skin; and
   at least one electrically insulating layer, covering at least a portion of the electrically conductive layer.

3. The method of claim 1, wherein the step of attaching the module to the electrode further comprises the step of attaching the module to the electrode using one or more of ferromagnetic/electrically conductive discs, conductive buttons, conductive leads, conductive tabs, conductive hooks, conductive snaps, conductive adhesive, and hook and loop fastener to allow transmission of vibration and electrical energy.

4. The method of claim 1 further comprising the steps of:
inputting a control signal to the module to control the intensity and duration of the electrical stimuli and vibration; and
controlling intensity and duration of the electrical stimuli and vibration using a controller in the module.

5. The method of claim 4, further comprising the steps of:
initially ramping up one or more of electrical stimuli and vibration using the controller, to avoid surprising the patient;
generating randomly timed bursts of one or more of electrical stimuli and vibration to distract the patient from the procedure; and
automatically generating, using the module, electrical energy and vibration when connected to the electrode and automatically discontinuing generation of electrical energy and vibration when not in use.

6. The method of claim 4, further comprising the step of indicating, using an LED, at least one or more of the status of the controller, battery status, operation of the electrical and vibration stimuli and patient physiology.

7. The method of claim 4, further comprising the step of displaying on a display, at least one or more of the status of the controller, battery status, operation of the electrical and vibration stimuli and patient physiology.

8. The method of claim 4, further comprising the step of generating one or more of a light display and sounds, for distracting the patient during the procedure.

9. The method of claim 1, wherein the access point comprises an orifice, wherein the step of attaching the electrode further comprises the step of:
inserting an object through the orifice and puncturing the patient's skin, such that the electrode surrounds the object and provides electrical and vibration stimuli to mask pain signals in the patient's skin.

10. An apparatus for providing topical analgesia during a procedure, comprising:
an electrode for attaching to a patient's skin, the electrode having one or more conductive surfaces and one or more access points for allowing objects to pass through the access point and into the patient's skin;
a module, attachable to the electrode, for generating electrical energy in order to deliver an electrical stimuli through the electrode and to the patient's skin to provide an analgesic effect; and
a flap, hinged to the electrode, acting as a bandage dressing by flipping down over the one or more access points after the procedure is completed, wherein the electrode and flap remain on the patient to act as a bandage,
wherein the electrode adheres to the patient's skin and the electrical stimuli act to mask pain signals caused when the objects penetrate the patient's skin.

11. The apparatus of claim 10, wherein the electrode comprises:
at least one electrically conductive layer for conducting the electrical stimuli from the module;
at least one electrically conductive adhesive layer, for adhering the electrically conductive layer to the patient's skin; and
at least one electrically insulating layer, covering at least a portion of the electrically conductive layer.

12. The apparatus of claim 10, further comprising attachment means for attaching the module to the electrode, the attachment means comprising one or more of ferromagnetic/electrically conductive discs, conductive buttons, conductive leads, conductive tabs, conductive hooks, conductive snaps, conductive adhesive, and hook and loop fastener, to allow transmission of electrical energy.

13. The apparatus of claim 10 wherein the module includes:
a controller for controlling intensity, timing, and duration of the electrical stimuli; and
an input means for inputting a control signal to control the intensity and duration of the electrical stimuli.

14. The apparatus of claim 13, wherein the controller initially ramps up electrical stimuli, generates randomly timed bursts of electrical stimuli, and automatically actuates the module to generate electrical energy when connected to the electrode and automatically actuates the module to discontinue generation of electrical energy when not in use.

15. The apparatus of claim 13, wherein the module further comprises an LED for indicating at least one or more of the status of the controller, battery status, operation of the electrical stimuli, and patient physiology.

16. The apparatus of claim 13, wherein the module further comprises a display for displaying at least one or more of the status of the controller, battery status, operation of the electrical stimuli, and patient physiology.

17. The apparatus of claim 13, wherein the module further comprises one or more of a light display and a sound generator, for distracting the patient during the procedure.

18. The apparatus of claim 10, wherein the access point comprises a window formed in the electrode, for allowing insertion of an object for puncturing the patient's skin, such that the electrode surrounds the object and provides electrical stimuli to mask pain signals in the patient's skin.

19. An apparatus for providing topical analgesia during a procedure, comprising:
(a) an electrode comprising:
(i) a non-conductive backing layer;
(ii) an electrically conductive layer positioned against the non-conductive backing layer, the electrically conductive layer comprising a first conductive surface and a second conductive surface;
(iii) an insulation component disposed between the first conductive surface and the second conductive surface;
(iv) an electrically conductive adhesive layer positioned against the electrically conductive layer, the electrically conductive adhesive layer comprising a first conductive adhesive surface positioned against the first conductive surface and a second conductive adhesive surface positioned against the second conductive surface, wherein the electrically conductive adhesive layer is configured to be adherable to a patient's skin;
(v) at least one access point defined in the electrode, the at least one access point configured to allow objects to pass through the access point and into the patient's skin; and
(b) a stimulation module attachable to the electrode, the stimulation module configured to generate stimuli to mask the pain signals caused when objects penetrate the patient's skin; and
(c) a flap hingedly coupled to the non-conductive backing layer, the flap configured to move between an open position and a closed position wherein the flap is disposed over the at least one access point.

20. The apparatus of claim 19, wherein the stimulation module comprises an electrical stimulation generating unit.

21. The apparatus of claim 19, wherein the stimulation module comprises a vibration stimulation generating unit.

22. The apparatus of claim 19, wherein the stimulation module comprises:
   (a) a transcutaneous electrical nerve stimulation ("TENS") generating unit configured to transmit electrical current to the electrode;
   (b) a vibration stimulation generating unit configured to transmit vibration energy to the electrode;
   (c) a controller operably coupled to the TENS generating unit and the vibration stimulation generating unit, the controller configured to control the TENS generating unit and the vibration stimulation generating unit; and
   (d) an input component operably coupled to the controller, the input component configured to allow a user to input a control signal to control intensity and duration of the electrical current and vibration energy.

23. The apparatus of claim 22, wherein the controller is further configured to initially gradually increase at least one of the electrical current and the vibration energy, generate randomly timed bursts of at least one of the electrical current and the vibration energy, automatically turn the apparatus on when the electrode and the module are coupled, and automatically shut off the apparatus when not in use.

24. The apparatus of claim 19, further comprising an attachment structure attachedly disposed between the stimulation module and the electrode, the attachment structure comprising one or more of ferromagnetic/electrically conductive discs, conductive buttons, conductive leads, conductive tabs, conductive hooks, conductive snaps, conductive adhesive, and hook and loop fastener, wherein the attachment structure is configured to allow transmission of vibration and electrical energy from the module to the electrode.

25. The apparatus of claim 19, wherein the stimulation module further comprises a display configured to display at least one of a status of the controller, battery status, operation of the electrical and vibration stimuli, and patient physiology.

26. The apparatus of claim 19, wherein the stimulation module further comprises at least one of a light display and a sound generator, wherein the light display and the sound generator are configured to distract the patient during the procedure.

27. The apparatus of claim 19, wherein the access point comprises an orifice, wherein the orifice has a circular, rectangular, or oval shape.

28. The apparatus of claim 19, wherein the access point comprises a notch.

* * * * *